United States Patent
Netto et al.

(10) Patent No.: US 9,679,757 B2
(45) Date of Patent: Jun. 13, 2017

(54) LIQUID CHROMATOGRAPHY SYSTEMS AND METHODS

(71) Applicant: Waters Technologies Corporation, Milford, MA (US)

(72) Inventors: Jeremy D. Netto, Singapore (SG); Mark Ritchie, Singapore (SG)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/248,662

(22) Filed: Apr. 9, 2014

(65) Prior Publication Data

US 2014/0306105 A1   Oct. 16, 2014

Related U.S. Application Data

(60) Provisional application No. 61/811,387, filed on Apr. 12, 2013.

(51) Int. Cl.
G01N 30/46   (2006.01)
G01N 30/20   (2006.01)
(Continued)

(52) U.S. Cl.
CPC .............. *H01J 49/26* (2013.01); *G01N 30/08* (2013.01); *G01N 30/461* (2013.01);
(Continued)

(58) Field of Classification Search
CPC ...... G01N 30/46; G01N 30/38; G01N 30/461; G01N 30/462; G01N 30/463;
(Continued)

(56) References Cited

U.S. PATENT DOCUMENTS 5,117,109 A * 5/1992 Asakawa ............. G01N 30/728
                                                     210/198.2
6,344,172 B1 * 2/2002 Afeyan et al. .................. 422/70
(Continued)

OTHER PUBLICATIONS

Gil et al. UPLC-MS metabolic profiling of second trimester amniotic fluid and maternal urine and comparison with NMR spectral profiling for the identification of pregnancy disorder biomarkers. Mol. BioSyst., 2012, 8, 1243-1254.*
(Continued)

*Primary Examiner* — Katherine Zalasky
(74) *Attorney, Agent, or Firm* — Locke Lord LLP; Nicholas J. DiCeglie, Jr.

(57) ABSTRACT

One aspect of the invention provides a liquid chromatography system including: a first solvent manager configured to dispense various ratios of a first solvent and a second solvent; a first column in fluid communication with the first solvent manager; a mixer in fluid communication with the first column; a first valve in fluid communication with the mixer; a second column having a first end in fluid communication with a first port of the first valve and a second end in fluid communication with a second port of the first valve; a second solvent manager adapted and configured to dispense various ratios of a third solvent and a fourth solvent; and a second valve in fluid communication with the second solvent manager, the first valve, and the mixer. The first valve and the second valve are adapted and configured for actuation between and a second position. In the first position: solvent dispensed by the first solvent manager and an injected sample flow over the first column; eluent from the first column is mixed with solvent dispensed by the second solvent manager in the mixer to produce a combined mobile phase; and the combined mobile phase is passed through the first valve and over the second column in a first direction to trap analytes of interest on the first column. In the second
(Continued)

position, solvent dispensed by the second solvent manager is passed over the second column in a second direction to release the analytes of interest from the second column.

7 Claims, 4 Drawing Sheets (51) Int. Cl.
*G01N 30/72* (2006.01)
*G01N 30/38* (2006.01)
*G01N 30/40* (2006.01)
*B01D 15/18* (2006.01)
*B01D 15/16* (2006.01)
*B01D 15/14* (2006.01)
*B01D 15/30* (2006.01)
*B01D 15/32* (2006.01)
*H01J 49/26* (2006.01)
*G01N 30/08* (2006.01)
G01N 30/04 (2006.01)
G01N 30/34 (2006.01)

(52) U.S. Cl.
CPC ......... *G01N 30/462* (2013.01); *G01N 30/463* (2013.01); *G01N 30/468* (2013.01); *G01N 30/7233* (2013.01); *B01D 15/14* (2013.01); *B01D 15/166* (2013.01); *B01D 15/1864* (2013.01); *B01D 15/1871* (2013.01); *B01D 15/1878* (2013.01); *B01D 15/305* (2013.01); *B01D 15/325* (2013.01); *G01N 30/72* (2013.01); *G01N 2030/085* (2013.01); *G01N 2030/201* (2013.01); *G01N 2030/202* (2013.01); *G01N 2030/347* (2013.01); *G01N 2030/382* (2013.01); *G01N 2030/385* (2013.01); *G01N 2030/388* (2013.01)

(58) Field of Classification Search
CPC .... G01N 30/468; G01N 30/20; G01N 30/482; G01N 30/72; G01N 30/7233; G01N 2030/382; G01N 2030/385; G01N 2030/388; G01N 2030/202; G01N 2030/201; G01N 2030/484; B01D 15/18; B01D 15/1864; B01D 15/1871; B01D 15/1878; B01D 15/166; B01D 15/14; B01D 15/305; B01D 15/30; B01D 15/325
See application file for complete search history.

(56) References Cited

U.S. PATENT DOCUMENTS

| | | | |
|---|---|---|---|
| 2003/0168392 A1* | 9/2003 | Masuda et al. | 210/198.2 |
| 2005/0167348 A1* | 8/2005 | Iwata | G01N 30/08 |
| | | | 210/198.2 |
| 2005/0218055 A1* | 10/2005 | Hayashi et al. | 210/198.2 |

OTHER PUBLICATIONS

Want et al. Global metabolic profiling procedures for urine using UPLC-MS. Nature Protocols, vol. 5, No. 6 (2010) 1005-1018.*

Lisa et al. Lipidomic profiling of biological tissues using off-line two-dimensional high-performance liquid chromatography-mass spectrometry. Journal of Chromatography A, 1218 (2011) 5146-5156.*

* cited by examiner

LIQUID CHROMATOGRAPHY SYSTEMS AND METHODS

CROSS REFERENCE TO RELATED APPLICATIONS

This application claims the benefit of priority of U.S. Provisional Patent Application No. 61/811,387, filed Apr. 12, 2013, the disclosure of which is expressly incorporated herein by reference thereto.

BACKGROUND

Lipids play many important roles in maintaining homeostasis of living organisms. An understanding these lipids could further our understanding into mechanisms of disease, including the identification of biomarkers and potential drug targets. Biofluids (e.g., plasma) are typically complex with large lipid diversity across many orders of concentration, which presents analytical challenges. Reverse-phase chromatography separates lipids based on their hydrophobicity, however shows no class distinction. Normal-phase and HILIC chromatography provides a separation based upon lipid head group, but provides little separation within a given class.

SUMMARY OF THE INVENTION

One aspect of the invention provides a liquid chromatography system including: a first solvent manager adapted and configured to dispense various ratios of a first solvent and a second solvent; a first column in fluid communication with the first solvent manager, a mixer in fluid communication with the first column; a first valve in fluid communication with the mixer; a second column having a first end in fluid communication with a first port of the first valve and a second end in fluid communication with a second port of the first valve; a second solvent manager adapted and configured to dispense various ratios of a third solvent and a fourth solvent; and a second valve in fluid communication with the second solvent manager, the first valve, and the mixer. The first valve and the second valve are adapted and configured for actuation between and a second position. In the first position: solvent dispensed by the first solvent manager and an injected sample flow over the first column; eluent from the first column is mixed with solvent dispensed by the second solvent manager in the mixer to produce a combined mobile phase; and the combined mobile phase is passed through the first valve and over the second column in a first direction to trap analytes of interest on the first column. In the second position, solvent dispensed by the second solvent manager is passed over the second column in a second direction to release the analytes of interest from the second column.

This aspect of the invention can have a variety of embodiments. The second column can be a trapping column. The first column can be a HILIC column.

The system can further include a third column in fluid communication with the first valve. The solvent dispensed by the second solvent manager and the analytes of interest eluted off of the second column can be passed over the third column. The third column can be a reversed-phase analytical column. The third column can be an HSS T3 column. Eluent from the third column can be presented to a mass spectrometer for analysis.

The first solvent manager can be adapted and configured to, while the first valve and the second valve are in the first position, shift from dispensing the first solvent to dispensing the second solvent. The first solvent can have high organic phase content. The second solvent can have high aqueous phase content.

The second solvent manager is adapted and configured to: while the first valve and the second valve are in the first position, dispense the third solvent; and, while the first valve and the second valve are in the second position, modulate from dispensing the third solvent to dispense increasing ratios of the fourth solvent. The third solvent can have high aqueous phase content. The fourth solvent can have high organic phase content.

Another aspect of the invention provides a method of liquid chromatography. The method includes: initiating a first solvent flow over a first column; initiating a second solvent flow having a high aqueous phase content; mixing an eluent from the first column with the second solvent flow to produce a combined mobile phase; passing the combined mobile phase over a second column in a first direction; and passing the second solvent flow over the second column in a second direction. The first solvent flow initially has high organic phase content.

This aspect of the invention can have a variety of embodiments. The method can include injecting a sample into the first solvent flow. The method can include shifting the first solvent flow from high organic phase content to high aqueous phase content. The high organic phase content can consist essentially of 10 mM ammonium acetate (having a pH of 8.0) in a 95:5 (V/V) ratio of acetonitrile to water. The high aqueous phase content can consist essentially of 10 mM ammonium acetate (having a pH of 8.0) in a 95:5 (V/V) ratio of acetonitrile to water.

Another aspect of the include shifting the second solvent flow from high aqueous phase content to high organic phase content. The high aqueous phase content can consist essentially of 10 mM ammonium acetate (having a pH of 5.0) in a 40:60 (V/V) ratio of acetonitrile to water. The high organic phase content can consist essentially of 10 mM ammonium acetate (having a pH of 5.0) in a 10:90 (V/V) ratio of acetonitrile to water.

Eluent from the second column can be passed over a third column. Eluent from the third column can be presented to a detector for analysis. The detector can be a mass spectrometer.

FIGURES

Aspects of the present disclosure can be better understood with reference to the following drawings. Components of the drawing are not necessarily to scale, emphasis instead being placed upon clearly illustrating the principles of the present disclosure. Moreover, the drawings, like reference numerals designate corresponding parts throughout the several views.

DEFINITIONS

The instant invention is most clearly understood with reference to the following definitions:

As used in the specification and claims, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein, the terms "comprises," "comprising," "containing," "having," and the like can have the meaning ascribed to them under U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION

Both normal-phase and reversed-phase methods have disadvantages.

Although reversed-phase based separation methods provide good separation of lipids, complete separation of lipids by class has not been shown. This is due to the fact that the mechanism of action in reversed-phase chromatography of lipids is based on their lipophilicity, which in turn is governed by the carbon chain length and the number of double bonds. As a consequence, co-elution of lipids belonging to different classes in reversed-phase separations is quite common.

Normal-phase methods including HILIC methods typically allow separation and characterization of different lipid classes but peak capacity and dynamic range suffers because of the large number of the same species lipids that elute within a short time frame, approximately 1 minute per lipid class.

With lipidomics as an application example, each lipid class eluting off the HILIC column could then further separated on the reversed-phase column according to their alkyl chain length, but eliminating the problem of co-elution of lipids belonging to different classes as described above.

Utilizing the advantages of both reverse-phase chromatography and normal-phase and HILIC chromatography in a combined two-dimensional high-performance liquid chromatography method benefits lipid research by providing a rapid method for use with mass spectrometry that tackles both complexity and dynamic range issues.

Unlike two-dimensional chromatography technologies, embodiments of the invention are based on a standard ultra-high pressure liquid chromatography (UHPLC) model and utilize a trapping column between the first and second dimension columns to act as a holding and focusing point for analytes eluting off the first dimension column.

Liquid Chromatography Systems

Figure 1A:
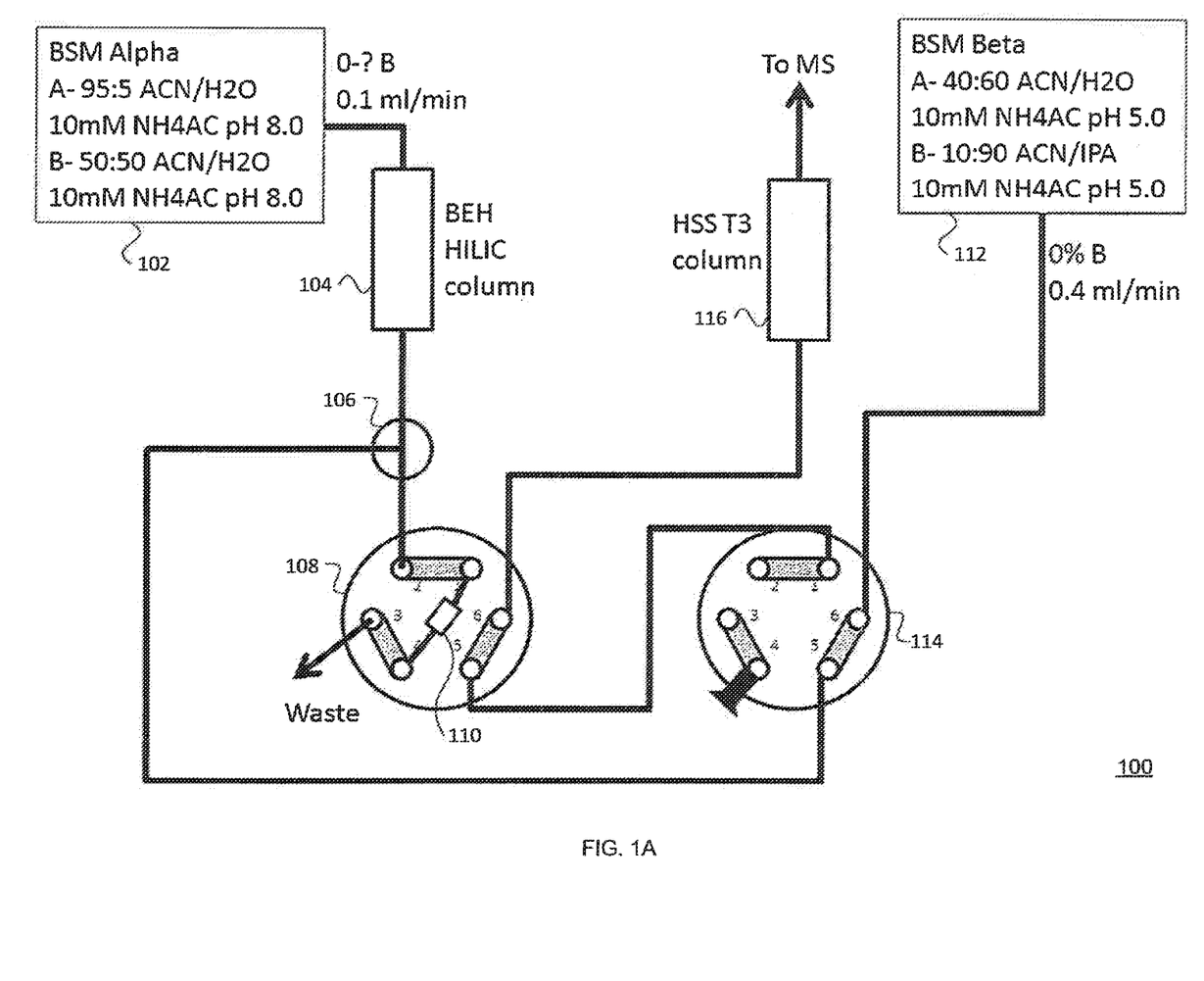
FIG. 1A depicts a liquid chromatography system 100 in a first position according to an embodiment of the invention.

Referring now to FIG. 1(a), one aspect of the system provides a liquid chromatography system 100 including a first solvent manager 102, a first column 104 in fluid communication with the first solvent manager 102; a mixer 106 in fluid communication with the first column 104, a first valve 108 in fluid communication with the mixer 106, a second column 110 having a first end in fluid communication with a first port of the first valve 108 and a second end in fluid communication with a second port of the first valve 108, a second solvent manager 112, and a second valve 114 in fluid communication with the second solvent manager 112, the first valve 108, and the mixer 106.

First solvent manager 102 and second solvent manager 112 are adapted and configured to dispense various ratios of one or more solvents. For example, solvent managers 102, 112 can be adapted and configured to solely dispense a single solvent at a given point in time or can dispense a blend of several solvents. The composition of this blend can be varied either in a continuous manner (e.g., changing from 100% of solvent A to a 50%/50% blend of solvents A and B over one minute) or in discrete steps (e.g., increasing the fraction of solvent B by 5% every minute). In some embodiments, the solvent managers 102, 112 are binary solvent managers. Suitable binary solvent managers (BSMs) are available from Waters Technologies Corporation of Milford, Mass.

Mixer 106 can be a high-pressure mixer capable of mixing two or more fluids at elevated pressures. In some embodiments, mixer 106 has a volume of about 50 µL. Suitable mixers are described in U.S. Patent Application Publication No. 2009/0294344.

First valve 108 and second valve 114 can be standard six-port, two-position valves as used the liquid chromatography industry. Such valves are available from Valve Instruments Co. Inc. of Brockville, Ontario and under the NANO-PEAK™ trademark from Scivex, Inc. of Oak Harbor, Wis.

First column 104 can, in some embodiments, be a hydrophilic interaction liquid chromatography (HILIC) column. In some embodiments, the first column is an ethylene bridged hybrid (HEB) column. Suitable columns are available under the ACQUITY® trademark from Waters Technologies Corporation of Milford, Mass.

Second column 110 can, in some embodiments, be a trapping column. Such columns can, for example, be high-strength silica columns. Suitable columns are available under the ACQUITY® and VANGUARD™ trademarks from Waters Technologies Corporation of Milford, Mass. In some embodiments, the dimensions of the second column 110 can be 2.1 mm×5 mm×1.7 µm.

System 100 can also include a third column 116. Third column 116 can, in some embodiments, be an ACQUITY® UPLC® HSS T3 (High Strength Silica with T3-trifunctional bonding) column available from Waters Technologies Corporation of Milford, Mass.

Operation of Liquid Chromatography Systems

Still referring to FIG. 1A, first valve 108 and second valve 114 are depicted in a first position. In this position, an injected sample is carried by the mobile phase from the first solvent manager 102 and passes through the first column 104, which is the first dimension column. The gradient running through the first column 104 is akin to normal-phase chromatography; that is, it begins with high organic phase content and gradually shifts to high aqueous phase content throughout the run time.

Simultaneously, the second solvent manager 112 will be pumping a mobile phase composition similar to that used on reversed-phase chromatography, i.e., having a high aqueous percentage. This flow path travels through position 6 to 5 of the second valve 114 and then is mixed with the eluent from the first column 104 in mixer 106. The flow rate from the first solvent manager 102 is kept constant at 0.1 mL/min and the flow rate from the second solvent manager 112 is kept constant at 0.4 mL/min. The eluent from the high pressure mixer 106 will have a 1:5 dilution of mobile phase from the first solvent manager 102 with mobile phase from second solvent manager 112. This new combined mobile phase will enter the first valve 108 at port 2. The flow path progresses from port 2 to port 1 to port 4 to port 3 to waste. Second column 110 is positioned between port 1 and port 4.

As a compound of interest elutes off the first column 104, it will be retained and focused on the second column 110. Retention of the compound on second column 110 can only be achieved if the compound has a higher affinity for the stationary phase than the mobile phase, but because of the high organic content of the eluent from the first column 104, there is a need to dilute it using solvent from the second solvent manager 112 in mixer 106 to order to raise the aqueous content before the second column 110.

Figure 1B:
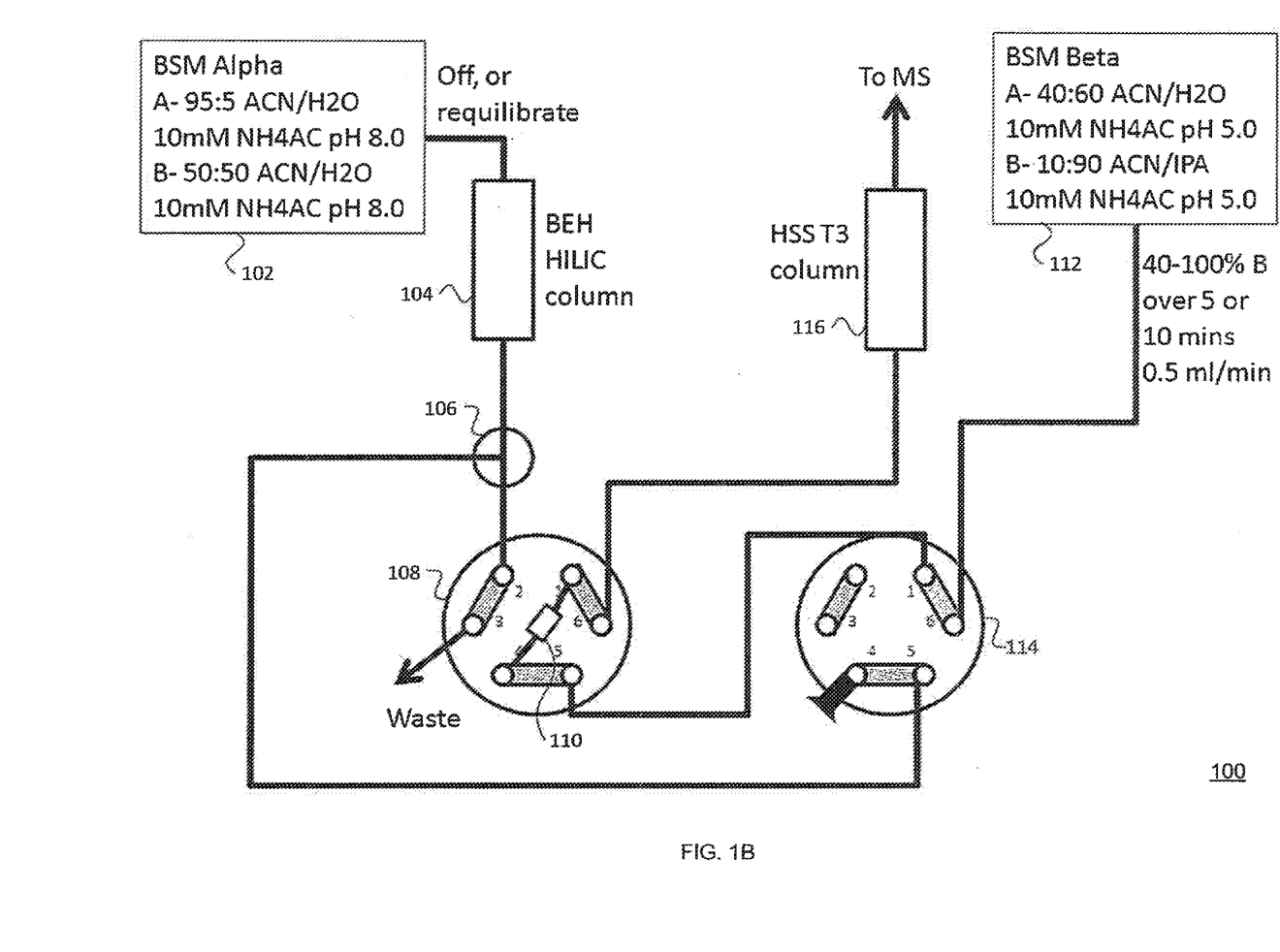
FIG. 1B depicts a liquid chromatography system 100 in a second position according to an embodiment of the invention.

Referring now to FIG. 1B, once the compound of interest is retained on the second column 110, both the first valve 108 and the second valve 114 switch to a second position. Upon switching, the flow rate of first solvent manager 102 can drop to 0 mL/min to hold the rest of the compounds in the first column 104 while the compound retained on the second column 110 is analyzed. In order to analyze the retained compound, solvent flows from the second solvent manager 112, to the second valve 114 at port 5, to the second valve 114 at port 1, to the first valve 108 at port 5, to the first valve 108 at port 4, to the second column 110, to the first valve 108 at port 1, to the first valve 108 at port 6, to the third column 116, and eventually to a mass spectrometer (MS) or other detector for analysis.

Once both valves 108, 114 are switched to the second position, a reversed-phase-type gradient ramp is commenced starting with high aqueous phase content and gradually shifting to high organic phase content throughout the run time. It should be noted that the flow path on the second column 110 is now reversed when compared to when the valves 108, 114 were in the first position. By increasing the organic content through this reverse-phase gradient from the second solvent manager 112, the compound 'back flushes' off the second column 110 into the third column 116 for further analytical separation and then to the MS for detection.

After the compound of interest is detected on the MS, the third column 116 undergoes a wash and equilibration stage similar to conventional single dimension chromatography, which prepares the third column 116 for the next sample. At the end of the third column's equilibration time, both valves 108, 114 switch back to the first position and the flow on first solvent manager 102 is restarted to 0.1 mL/min (from the last stopped gradient) to elute the next compound of interest off the first column 104 to be retained in the second column 110. The process of switching to the valves 108, 114 back and forth between the first position and the second position for each compound of interest described is repeated until all the compounds of interest are analyzed by the MS.

Methods of Liquid Chromatoarahy

Figure 2:
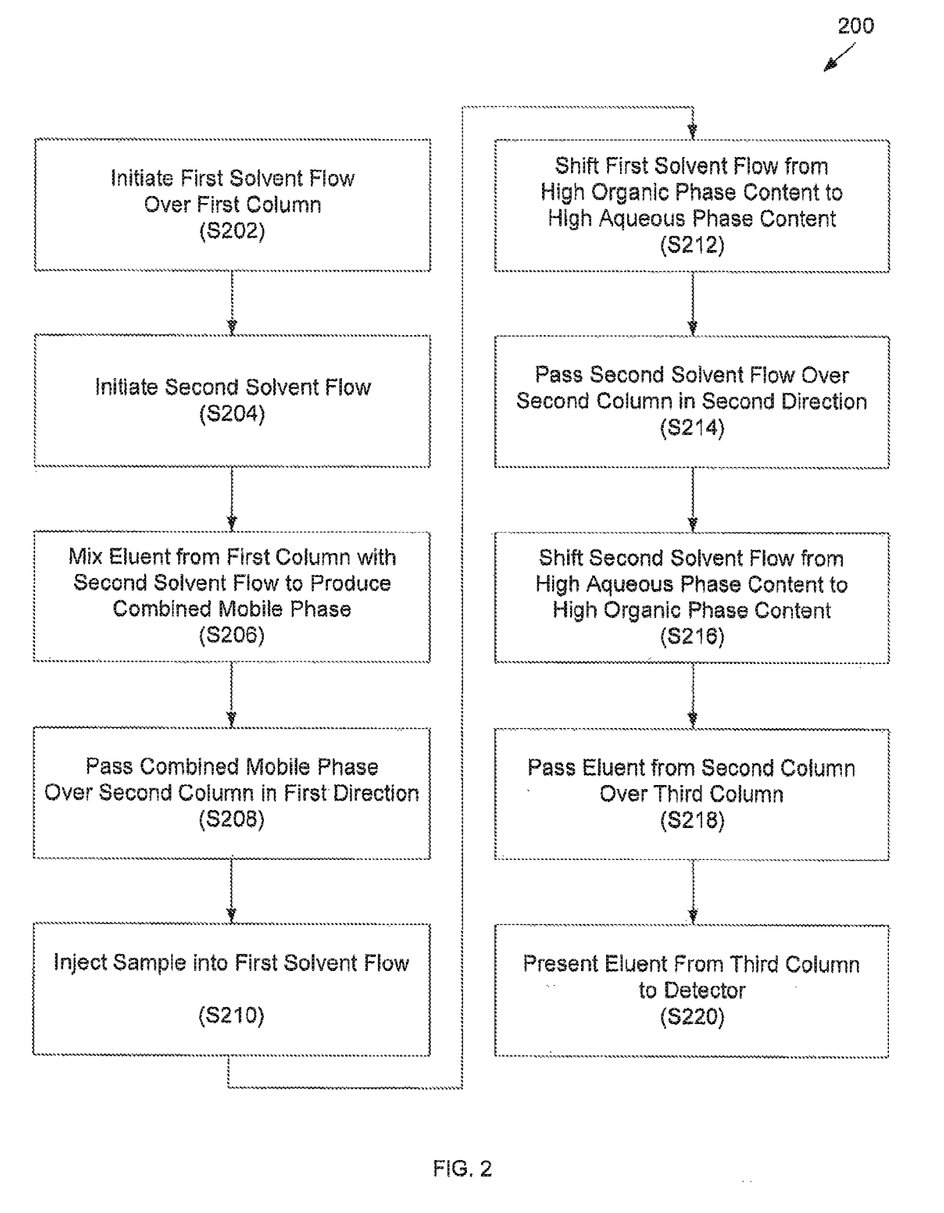
FIG. 2 depicts a method of liquid chromatography 200 according to an embodiment of the invention.

Referring now to FIG. 2, it should be appreciated that fluid flows described above in the context of FIGS. 1A and 1B are patentable regardless of how they are physically implemented. Accordingly, FIG. 2 provides a method of liquid chromatography 200.

In step S202, a first solvent flow over a first column is initiated. The first solvent flow can be initiated by a solvent manager as discussed herein. First column can be a column 104 as described herein. In one embodiment, the first solvent flow initially has a high organic phase content. For example, the first solvent flow can initially consist of a solution of 10 mM ammonium acetate (having a pH of 8.0) in a 95:5 (V/V) ratio of acetonitrile to water.

In step S204, a second solvent flow is initiated. The second solvent flow can be initiated by a solvent manager as discussed herein. In one embodiment, the second solvent flow initially has a high aqueous phase content. For example, the second solvent flow can initially consist of a solution of 10 mM ammonium acetate (having a pH of 5.0) in a 40:60 (V/V) ratio of acetonitrile to water.

In step S206, eluent from the first column is mixed with the second solvent flow to produce a combined mobile phase. Mixing can be facilitated by a mixer 106 as described herein.

In step S208, the combined mobile phase can be passed over a second column in a first direction. The second column can be column 110 as described herein.

In step S210, a sample can be injected into the first solvent flow using known methods and equipment in the field of liquid chromatography.

In step S212, the first solvent flow can be shifted from a high organic phase content to high aqueous phase content. This shift can be continuous. In one embodiment, the first solvent flow is shifted to a blending a solution of 10 mM ammonium acetate (having a pH of 8.0) in a 50:50 (V/V) ratio of acetonitrile to water with the solution of 10 mM ammonium acetate (having a pH of 8.0) in a 95:5 (V/V) ratio of acetonitrile to water initially provided in the first solvent flow.

In step S214, the second solvent flow is passed over the second column in a second direction. The second direction can be opposite the first direction.

In step S216, the second solvent flow can be shifted from a high aqueous phase content to high organic phase content. This shift can be continuous. In one embodiment, the second solvent flow is shifted to a blending a solution of 10 mM ammonium acetate (having a pH of 5.0) in a 10:90 (V/V) ratio of acetonitrile to water with the solution of 10 mM ammonium acetate (having a pH of 5.0) in a 40:60 (V/V) ratio of acetonitrile to water. For example, the second solvent flow can consist of between about 40% and about 100% of the high organic phase content solution.

In step S218, eluent from the second column is passed over a third column. Third column can be column 116 as discussed herein.

In step S220, eluent from the third column can be presented to a detector such as a mass spectrometer for analysis.

Working Example

Construction of Liquid Chromatography System

Figure 3:
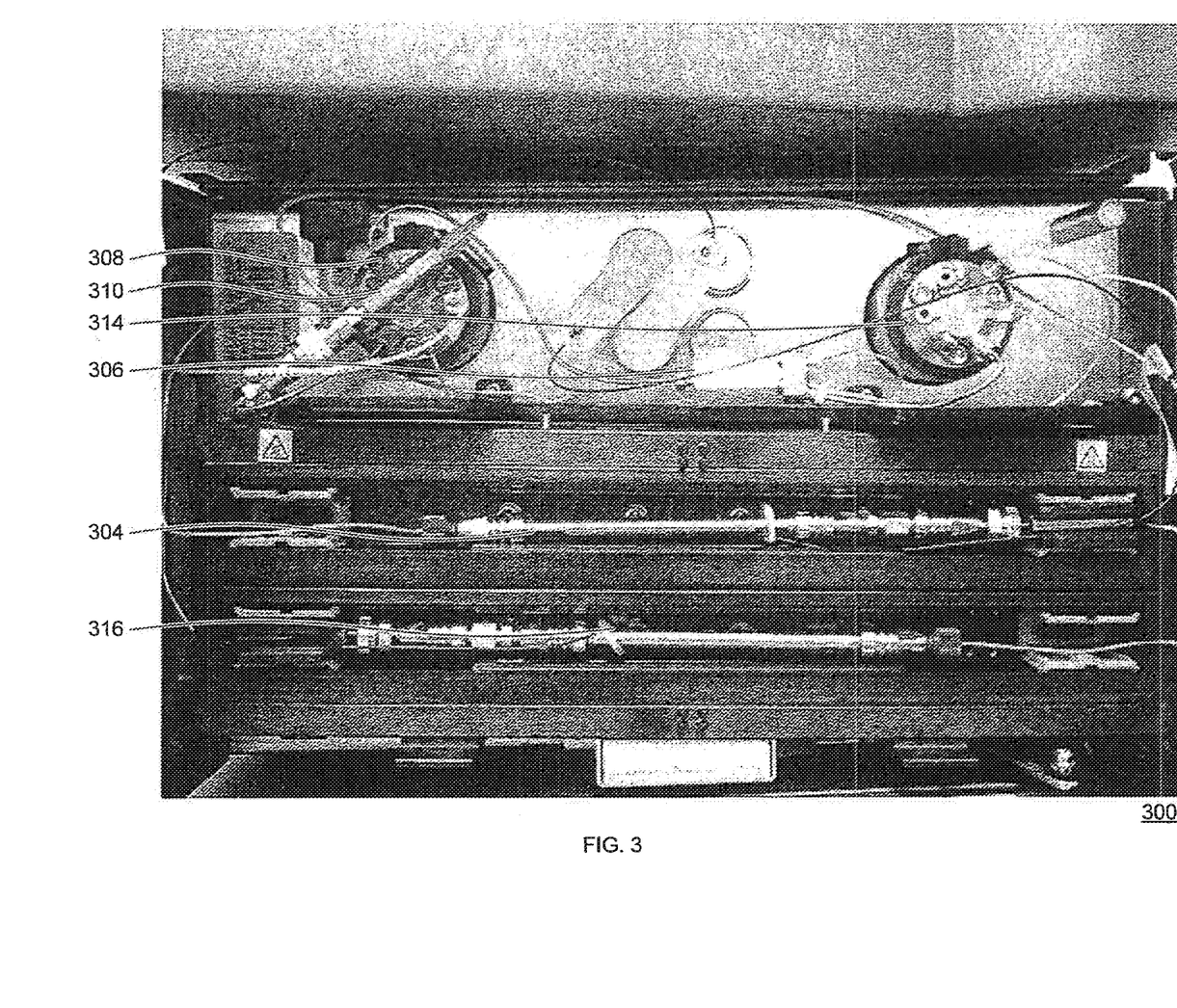
FIG. 3 depicts a working prototype of a liquid chromatography system 300 according to an embodiment of the invention.

Referring now to FIG. 3, a working liquid chromatography system 300 was constructed.

The system 300 included a first column 304, a mixer 306, a first valve 308, a second column 310, a second valve 314, and a third valve 316.

EQUIVALENTS

Although preferred embodiments of the invention have been described using specific terms, such description is for illustrative purposes only, and it is to be understood that changes and variations may be made without departing from the spirit or scope of the following claims.

The systems and methods described herein can be modified by changing the mobile phase composition (such as solvent composition, and additives such as salts, buffers and pH modifiers), pH, gradient (time, shape, relative percentages of solvents, etc.), column/packing material (size, chemistry, porous/non-porous, core-shell, etc.), temperature (sample, solvent, column), pressure and flow rate.

The systems and methods described herein are scalable and can, for example, be performed by a NANOAQUITY UPLC® device available from Waters Technologies Corporation of Milford, Mass.

The systems and methods described herein are also amenable to fraction collection (either time fractions or class separated fractions), collected either manually or automated. These fractions can then be analyzed by MALDI or used for further separation (off-line 2D LC). The systems and methods described herein can also be combined with other steps of chromatography as part of a multi-dimensional (UP)LC separation method, for example HILICxRP, either on-line or off-line (following fraction collection, as described), or other separation methods, such as ion mobility.

This systems and methods described herein can be employed on any combination of a UPLC® system, a UHPLC system, and an MS system, and can include any number of stages of MS. The HILIC column can use any polar solid phase surface chemistry, including, but not restricted to simple silica silanol or diol, amino or anionic, amide, cationic or zwitterionic, and bound to any type of packing material, e.g., monolithic, porous, solid, pellicular (fused/solid-core, semiporous) or composite beads.

The systems and methods described herein can be applied to any sample containing plasmalogens and other glycerophospholipids, including biological fluids such as plasma, serum, urine, but also extracts from cells and tissue (particularly neural) including bacteria, plants and fungi.

By re-plumbing the system (flow path), applications needing "filter" trapping, trap and back transfer, heart cutting, parallel column regeneration and at-column dilution can be performed.

Additionally, by utilizing the arrangement depicted and described in the context of FIGS. 1A and 1B, but changing the combination of the three columns to other chemistries currently available from Waters Technologies Corporation would give rise to other forms of multi-dimensional UPLC® systems not described before in literature. This includes, but is not limited to reversed-phase—size exclusion chromatography, ion exchange—reversed-phase chromatography, temperature rising elution fractionation—size exclusion chromatography, etc.

As an alternative to the separation of polar compounds using HILIC as the first column 104 described above, supercritical fluid chromatography can be used instead. For this system proposed, an Ultra Performance Supercritical Fluid Chromatograph (UPSFC) available under the WATERS® UPC2 mark from Waters Technologies Corporation of Milford, Mass. can be coupled to an existing UPLC® system and be used as the first dimension of separation. In this configuration, eluent from the UPC2® system will be directed to the trap column and operation for trapping and second dimension separation will be similar to that depicted and described in the context of FIGS. 1A and 1B.

INCORPORATION BY REFERENCE

The entire contents of all patents, published patent applications, and other references cited herein are hereby expressly incorporated herein in their entireties by reference.

The invention claimed is:

1. A liquid chromatography system comprising:
a first solvent manager adapted and configured to dispense various ratios of a first solvent and a second solvent;
a first HILIC column in fluid communication with and downstream of the first solvent manager;
a mixer in fluid communication with and downstream of the first column;
a first valve in fluid communication with and downstream of the mixer;
a second trapping column having a first end in fluid communication with a first port of the first valve and a second end in fluid communication with a second port of the first valve such that flow between the first port and the second port passes through the second trapping column;
a second solvent manager adapted and configured to dispense various ratios of a third solvent and a fourth solvent; and
a second valve in fluid communication with and downstream of the second solvent manager, wherein the second valve is in fluid communication with and upstream of the first valve at a first port of the second valve, and wherein the second valve is in fluid communication with and upstream of the mixer at a second port of the second valve;
wherein the first valve and the second valve are adapted and configured for actuation between:
a first position in which the second solvent manager is in fluid communication with the mixer through the second valve and the second trapping column is in fluid communication with the mixer through the first valve such that:
solvent dispensed by the first solvent manager and an injected sample flow over the first column and provide a gradient of relatively higher to relatively lower organic concentration;
eluent from the first column in a high organic solution is mixed and diluted with solvent dispensed by the second solvent manager in the mixer to produce a combined mobile phase; and
the combined mobile phase is passed through the first valve and over the second trapping column in a first direction to trap analytes of interest on the first column; and
a second position in which the second solvent manager is not in fluid communication with the mixer but is in fluid communication with the second trapping column through both the second valve and the first valve such that:
solvent dispensed by the second solvent manager is passed over the second column in a second direction to release the analytes of interest from the second column.

2. The system of claim 1, further comprising:
a third column in fluid communication with the first valve, wherein the solvent dispensed by the second solvent manager and the analytes of interest eluted off of the second column are passed over the third column.

3. The system of claim 2, wherein the third column is a reversed-phase analytical column.

4. The system of claim 2, wherein the third column is an HSS T3 column.

5. The system of claim 2, wherein eluent from the third column is presented to a mass spectrometer for analysis.

6. The system of claim 1, wherein the first solvent manager is adapted and configured to, while the first valve and the second valve are in the first position, shift from dispensing the first solvent to dispensing the second solvent, wherein the first solvent has high organic phase content and wherein the second solvent has high aqueous phase content.

7. The system of claim 1, wherein the second solvent manager is adapted and configured to:
  while the first valve and the second valve are in the first position, dispense the third solvent, wherein the third solvent has high aqueous phase content; and
  while the first valve and the second valve are in the second position, modulate from dispensing the third solvent to dispense increasing ratios of the fourth solvent, wherein the fourth solvent has high organic phase content.

* * * * *